(12) United States Patent
Béland

(10) Patent No.: US 6,746,863 B2
(45) Date of Patent: Jun. 8, 2004

(54) STERILIZABLE PROBE FOR EXTRACTION OF VOLATILE COMPOUNDS IN LIQUIDS AND THEIR QUANTITATIVE DETERMINATION

(75) Inventor: Mario Béland, Laval (CA)

(73) Assignee: National Research Council of Canada, Ottawa ( * ) Notice: Subject to any disclaimer, the term of this patent is extended or adjusted under 35 U.S.C. 154(b) by 111 days.

(21) Appl. No.: 10/068,936

(22) Filed: Feb. 11, 2002

(65) Prior Publication Data

US 2003/0153068 A1 Aug. 14, 2003

(51) Int. Cl.[7] .................................................. C12M 1/34
(52) U.S. Cl. ..................... 435/287.1; 422/68.1; 422/83; 73/19.1; 73/23.41; 73/61.59
(58) Field of Search ............................... 73/19.01, 19.1, 73/23.41, 61, 59; 422/68.1, 83; 435/287.1

(56) References Cited

U.S. PATENT DOCUMENTS

| | | |
|---|---|---|
| 3,830,106 A | 8/1974 | Gardiner et al. ............ 210/321 |
| 4,869,873 A | 9/1989 | Klein et al. ................... 422/51 |
| 5,398,559 A | 3/1995 | Westlake, III et al. | 
| 5,979,219 A | 11/1999 | Sellmer-Wilsberg et al. ......................... 73/19.12 |

FOREIGN PATENT DOCUMENTS

EP        0 174 417 A       3/1986

OTHER PUBLICATIONS

Guarna, M.M. et al. 1997. On–line monitoring and control of methanol concentration in shake flask culture of *Pichia pastoris*, John Wiley & Sons, 279–286.

Yano, T. et al. 1978. Silicone tubing sensor for detection of methanol, J. Fermentation Technology, vol. 56, No. 4, 421–427.

Austin G.D. et al. 1992. Monitoring and control of methanol concentration during polysaccharide fermentation using an on–line methanol sensor. Bioprocess Bioengineering, vol. 7, 241–247.

"Development Of A Responsive Methanol Sensor And Its Appliction In Pchia Pastoris Fermentation" Xiang–Shan Zhou, et al, Biotechnology Lertters, 24: 643–646, 2002.

Primary Examiner—David A. Redding
(74) Attorney, Agent, or Firm—J. Wayne Anderson

(57) ABSTRACT

An improved tube probe for measuring volatile compounds in a liquid or gas contained in a reactor or in any other environment is disclosed. The probe is made of a single piece of metal, to one end of which is attached a gas permeable tubing, threaded on a supporting plate. The plate permits to use of a variety of tube lengths and diameters while protecting the tube from mechanical stress due to agitation and aeration. Furthermore, the plate gives the possibility to have a longer permeable tube than the single loop probe approach. The probe is designed so that when in use, substantially only the tube is located inside the reactor. The volatile compounds permeate into the tube into the carrier gas and the carrier gas+volatiles mixture is carried to a detector through a channel provided in the probe body. The probe is economical to make and to maintain, while achieving high performance.

15 Claims, 4 Drawing Sheets

STERILIZABLE PROBE FOR EXTRACTION OF VOLATILE COMPOUNDS IN LIQUIDS AND THEIR QUANTITATIVE DETERMINATION

FIELD OF INVENTION

The invention resides in the field of quantitative determination of volatile compounds in liquids. In particular, the invention relates to an improved gas permeable tubing probe for measuring one or more volatile compounds in liquids or fluids.

BACKGROUND OF INVENTION

Gas sensors for determining the concentration of volatile compounds in liquids are in wide use in a variety of environments, e.g., chemical plants, solution agro-food plants, beverage industry, fermentation broths, etc. For example, the alcohol industry produces ethanol by fermentation while the biotechnology community uses methanol-oxidizing micro-organisms to produce either valuable research reagents or clinical/commercial products. Therefore, there is an increasing need for measuring, in real-time, methanol concentration or that of any other volatile of interest in fermentation broths or in any liquids in order to control that concentration and to prevent or minimize hazards. There are currently a few approaches, which are commonly used, to analyse volatile compounds in fermentation broth. One is to analyse exhausted gases in the non-sterile section of the fermenter and another one is to analyse the volatile(s) through the use of a carrier gas and of a permeable membrane or tubing made of silicone or PTFE (Teflon).

The first approach gives a very slow response regarding the concentration of the particular volatile and is sensitive to changes in the airflow rate, which makes control very difficult. This is often the case when the dissolved oxygen level is controlled by varying the aeration rate.

In the second approach, a probe made of a gas permeable tube is inserted into the fermentation broth. A carrier gas passing through the tube collects volatiles that pervaporate through the tube from the broth. A volatile detector is connected at the outlet of the tube to measure the concentration of the volatile(s) of interest. U.S. Pat. No. 5,204,262, Apr. 20, 1993, Meiering et al, describes an ethanol sensor for computerized fermentation control. It makes use of a rigid Teflon tubing mechanically tied between the inlet and outlet gas carrier ports. The ports are part of an empty rigid tube responsible for bringing the small carrier gas tube to the ports. In the patent, the probe consisting of a piece of tube is inserted from the top of the fermenter. This design, however, limits the use of the probe to small-scale fermenters and does contain a sealing mechanism to ensure sterility. None of the tubing probes presently available is compatible with the 25 mm port used with most fermenters.

U.S. Pat. No. 4,404,284, Sep. 13, 1993, Heider et al, presents a technique for measuring volatile constituents of a culture medium, in that a permeable membrane and a carrier gas are used. In the patent, the probe consists of a silicone membrane slid on to a cylindrical core whose exterior is provided with helical ducts. The silicone membrane and the helical ducts form a helical channel through which a carrier gas and volatiles are transported. The carrier gas containing the volatile(s) of interest is brought back to a sensor either inside or outside the body of the probe. The probe is made of two parts machined with precision that force the carrier gas in and out of the body. This probe works well and is compatible with 25 mm ports. The probe is, however, more complicated to build, more expensive and the membrane is very fragile. This constitutes a real problem whenever membrane perforation occurs and the contents of the fermenter, especially at the larger scales, must be thrown away causing important losses of money and time.

There is, therefore, a need for a sterilisable tubing probe that can be inserted in any port, including the 25 mm side port of common fermenters (bioreactors). The probe must be robust and easy to build, and must permit its use whatever the fermenter size, including pilot plant fermenters (20L to 1500L, or more).

SUMMARY OF INVENTION

In accordance with one aspect, the invention provides a volatile extraction probe designed in such a way that it can be inserted into a fermenter. The probe has a body made of a single piece of metal joined with a perforated plate supporting a piece of gas permeable tube of varying length for transporting a carrier gas and the volatile(s) of interest from the fermenter to the outside.

In accordance with another aspect, the probe of the invention is designed so that substantially only the gas permeable tube is located inside the fermenter.

In accordance with still another aspect, the probe is operable with a variety of lengths of a gas permeable tube so that the probe can be optimized to suit volatile(s) of interest and operating conditions.

In accordance with still another aspect, the tube is threaded in and out of a supporting plate avoiding, therefore, any mechanical stress to the tube due to agitation or to aeration. This permits operation with a variety of lengths of a gas permeable tube so that the probe can be optimized to suit volatile(s) of interest and operating conditions.

In accordance with yet another aspect, the probe of the invention is easy and economical to manufacture due to a single body construction. It is also easy to maintain because it makes use of readily available silicone tubing of any length and diameter.

In accordance with yet another aspect, the probe of the invention is steriliable-in-place due to its sealing mechanism and easy but solid tubing attachment. The design of the body is made to fit in a standard 25 mm port but by redesigning the body section it can be easily adapted to other commonly found port (flanged, tri-clamp, threaded) in industry.

In accordance with a further aspect, the invention is directed to a tubing probe for measuring a volatile compound in a fluid contained in an enclosure. The probe comprises a probe body made of a single piece of metal and inlet and outlet channels provided in the probe body. The probe further includes a gas permeable tube attached to one end of the probe body to form a continuous passage for a carrier gas between the inlet and outlet channels, and a sealing mechanism between the enclosure and the probe body for positioning substantially only the gas permeable tube inside the enclosure so that when the probe is inserted into the enclosure, the volatile compound pervaporates into the gas permeable tube.

In accordance with a further aspect, the outlet of the probe, having a carrier gas enriched with the volatile compound(s), directs the carrier gas+volatiles mixture to the top center of the body where a sensor headset can be screwed on.

BRIEF DESCRIPTION OF DRAWINGS

It should be noted that in all the drawings and the following description, like parts are shown by like numerals.

DETAILED DESCRIPTION OF PREFERRED EMBODIMENTS OF INVENTION

Figure 1:
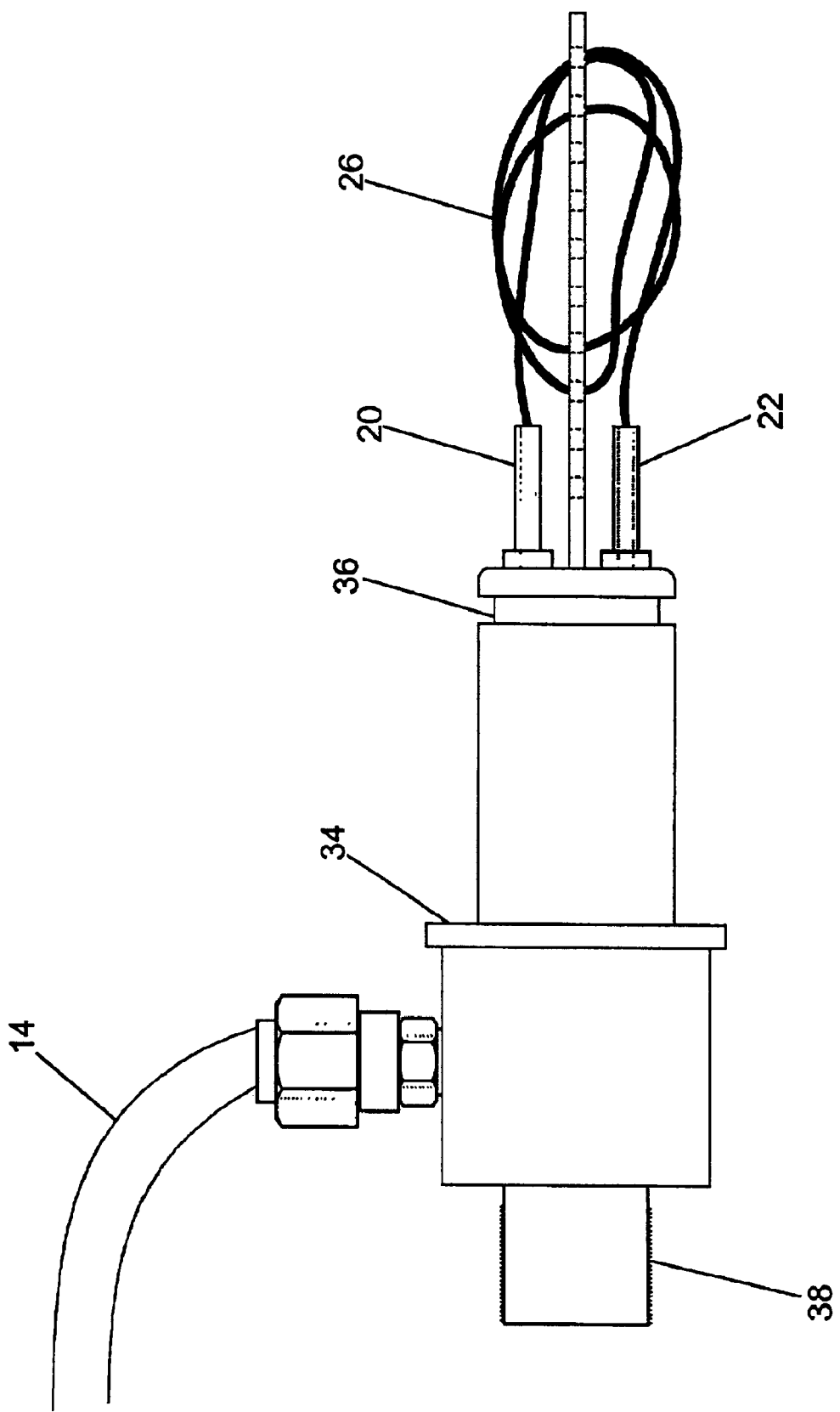
FIG. 1 is a surface view of the probe according to one embodiment.
Figure 2:
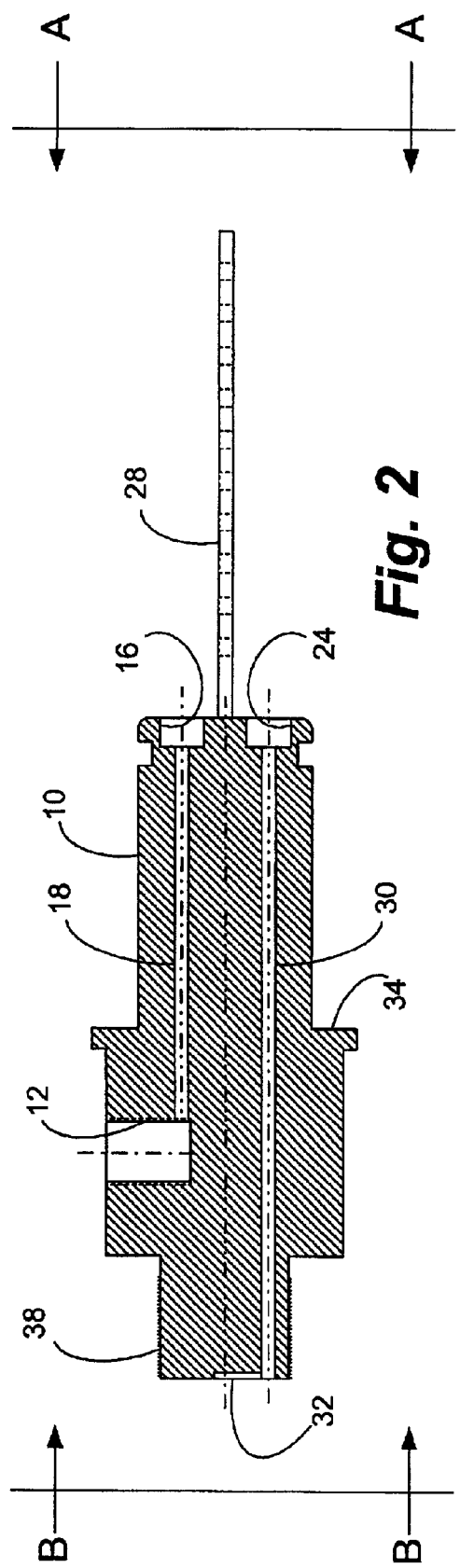
FIG. 2 is a lateral cross sectional view of the probe according to the same embodiment.
Figure 3:
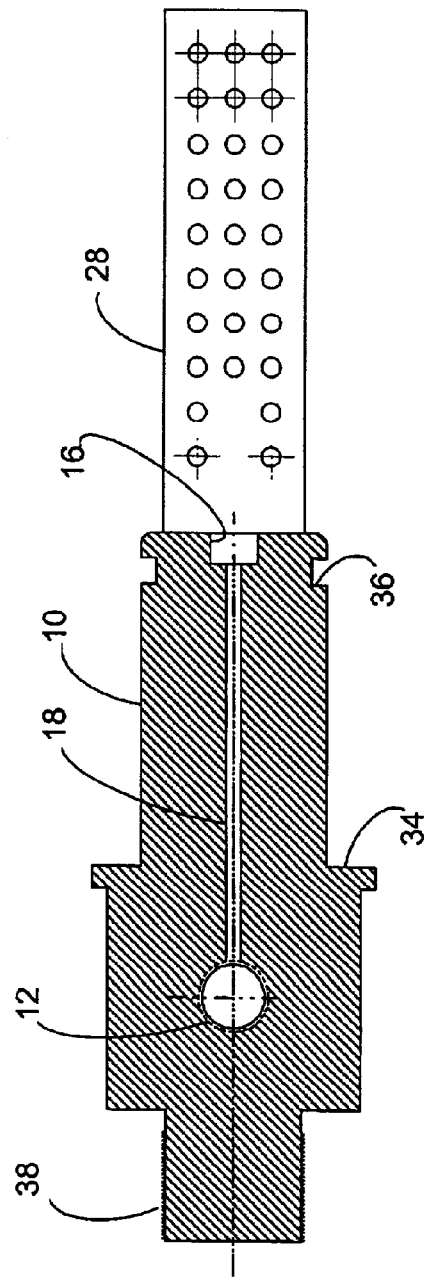
FIG. 3 is another lateral cross sectional view of the probe according to the same embodiment.
Figure 5:
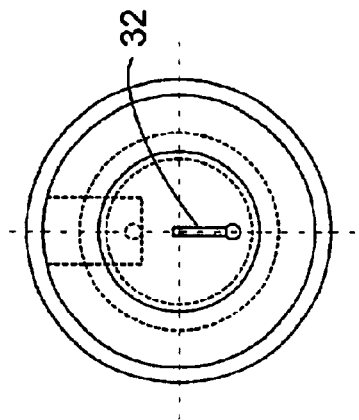
FIG. 5 is another side view taken in the direction B—B shown in FIG. 2.
Figure 6:
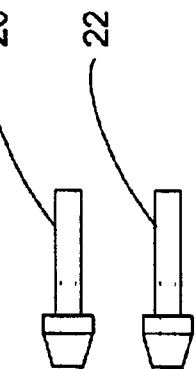
FIG. 6 is a plane view of tube adaptors according to one embodiment of the invention.
Figure 4:
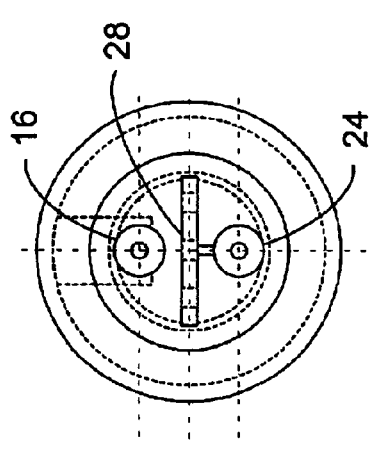
FIG. 4 is a side view taken in the direction A—A shown in FIG. 2.

FIGS. 1–5 show various views of the probe according to one embodiment of the invention. Referring to the figures, the probe body 10 is made of a single piece of metal in which one side port 12 is perforated with a standard NPT (National Pipe Thread) thread. This port serves as an inlet connection for a gas carrier supply tube 14. The carrier gas travels from side port 12 to an outlet port 16 of the body 10 through an inlet channel 18 drilled in the body. In the outlet port 16, a standard ⅛" tube adapter 20 is welded. Likewise, another ⅛" tube adapter 22 is also welded in a return port 24 provided on the body 10. The tube adaptors are shown in detail in FIG. 6, in which each adaptor is made of a two sections, one thinner section to receive a gas permeable tube (to be described below) and a thicker section to be welded to the probe body. Referring back to FIGS. 1–5, a piece of silicone tubing 26 of a given length is provided between the tube adaptors 20 and 22 by putting each end of the tubing firmly on each respective adaptor. The silicone tubing 26 is threaded onto a perforated plate 28. An output channel 30 is drilled through the probe body 10 to pass a flow of the carrier gas now containing a small proportion of the volatile(s) out of the probe to a measuring device (not shown), which may be connected to it.

Figure 7:
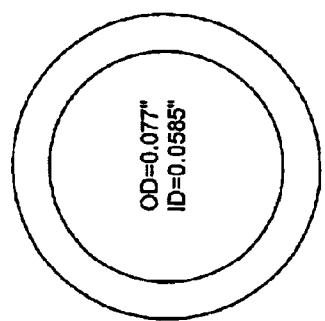
FIG. 7 is a cross sectional view of the tubing according to one embodiment of the invention.

To facilitate installation, the extremities of the silicone tubing are dipped for a few seconds in chloroform; this will soften and enlarge the silicone tubing. The tubing can thus be easily installed on the tube adapters. After evaporation of the chloroform, the silicone tubing comes back to its normal dry state and because its rest diameter is smaller than ⅛", it stays firmly in place. The diameter sizes of the tubing according to this embodiment are shown in FIG. 7. The silicone tubing may be cut to the desired length that suits the particular process in order to magnify sensitivity to the volatile(s) of interest. The supporting plate (perforated plate) 28, through which the silicone tubing is threaded, hangs the tubing firmly while permitting the use of pieces of tubing much longer than if it was only immersed free in the broth. The size of the supporting plate and the tubing diameter may also be adjusted to the fermenter size or for other considerations. The supporting plate can be made replaceable so that a plate of a desired size and desired holes can be fitted on the probe body for the optimal operation.

Figure 8:
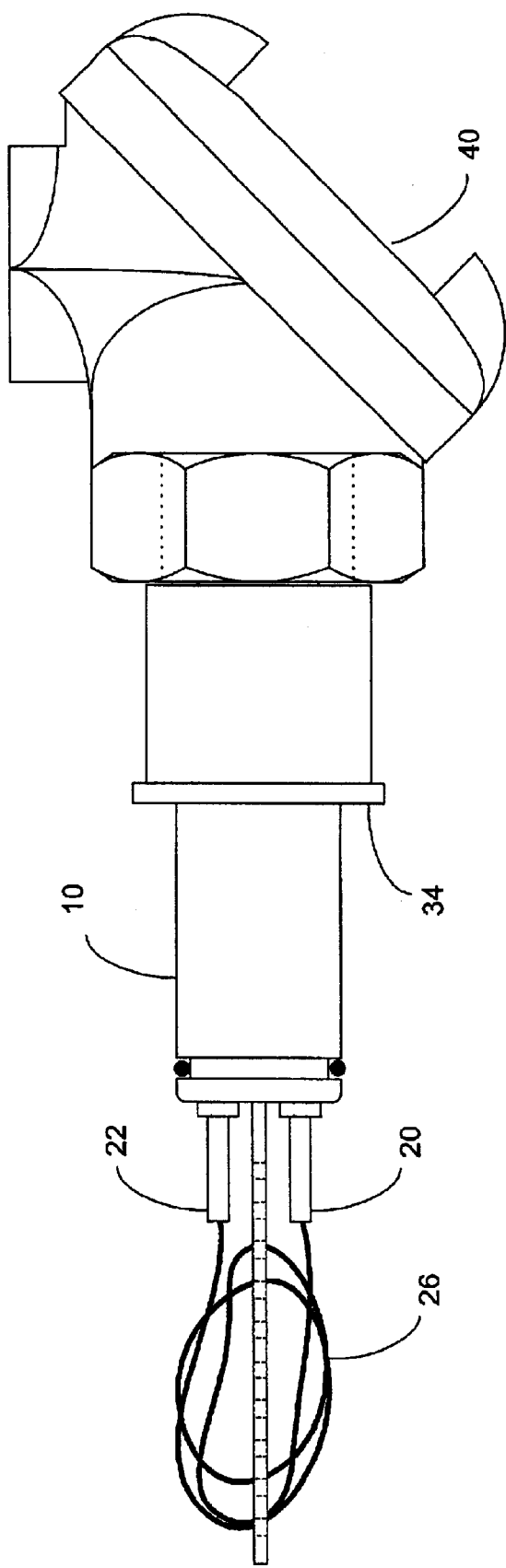
FIG. 8 is a plane view of the probe according to another embodiment of the invention, which is fitted with a detector head set.

A notch 32 present on the head of the probe is provided to send the carrier gas to the centre of the probe to which a measuring device is attached. This permits the use of a gasket on the headset without compromising flow circulation in the channel. The probe is maintained in place on/in the fermenter using a standard port nut pressing on the shoulder 34 which ensures that, when inserted, the probe stays firmly in place. It should be noted that the probe can be sized to match any port structure, including a standard 25 mm port, Tri-clamp, Flange port threaded port etc. An O-ring receptacle 36 is grooved on the body to assure sterility. The locations of the shoulder and O-ring ensure that the maximum length of tubing is located inside of the broth while maintaining sterility of the culture/fermenter. Specifically, when the probe is inserted through the wall hole of the fermenter, the O-ring in the receptacle 36 must seal between the probe body and the wall hole to ensure sterility. It is therefore clearly seen that the shoulder 34 resting on the exterior of the enclosure should ensure that the end of the probe body not be positioned very much inside the fermenter. This results in the maximum length of the tubing being located inside the broth. The head 38 of the probe is made of a standard thread permitting easy installation of the measuring device. For example, in another embodiment, as shown in FIG. 8, en industrial head set 40 compatible with the probe head 38 thread type may be adapted in order to place a direct reading sensor such as the methanol sensor Figaro TGS822 or other measuring devices.

The probe makes use of a carrier gas circulating through a gas permeable tube into which the volatile(s) pervaporate from the broth. The volatile(s) is transported out of the probe by the carrier gas to a detector that measures the concentration of the volatile(s) of interest. According to the invention, using a probe body made of a single piece of metal leads to reduction in the cost of manufacture and permits use of the probe with any fermenter size. Silicone tubing is inexpensive and may be purchased from many sources whereas the silicone membrane is harder to find and more expensive. The supporting plate ensures tubing stability and prevents mechanical stress while giving the possibility to increase tubing length. At the same time, the plate increases surface contact of the tube-liquid interface thus giving better mass transfer.

One probe prototype has been produced. Response tests have been done and the probe has passed the sterility test. The probe prototype has been compared to the membrane type probe already in place under fermentation conditions. The preliminary results have been positive but some fine-tuning still has to be done regarding optimal tubing length and carrier gas flowrate. The probe is as accurate as the membrane probe and shows good stability. A real fermentation where the probe will be the input source for methanol concentration monitoring and control has still to be realized.

The probe of the invention finds applications in a variety of fields and environments (chemical plants, agro-food industry, beverage industry, fermentation industry, etc.) where monitoring methanol or ethanol is conducted. The alcohol industry (producing ethanol by fermentation) and the biotechnology community (industrial and research community), which is increasingly using methanol-oxidizing microorganisms to produce either research reagents or clinical/commercial products, are two obvious end-users for this technology. Manufacturers of fermentation equipment (fermenters and peripherals) should be particularly interested in a probe of this type. Combined with the necessary sensor (semi-conductor) for the volatile(s) of interest, the probe of the invention is applicable to any situation involving volatile substances in a sterile or non-sterile environment.

What is claimed is:

1. A tubing probe for measuring a volatile compound in a fluid contained in an enclosure, comprising:
   a probe body made of a single piece of metal;
   inlet and outlet channels provided in the probe body;
   a gas permeable tube attached to one end of the probe body to form a continuous passage for a carrier gas between the inlet and outlet channels;
   a sealing mechanism between the enclosure and the probe body for isolation of inside of the enclosure, and
   the probe body having a shoulder for positioning the probe such that the body is outside the enclosure and the gas permeable tube is inside the enclosure when the shoulder is made to rest on the exterior of the enclosure so that when the probe is inserted into the enclosure from the outside, the volatile compound pervaporates into the gas permeable tube.

2. The tubing probe according to claim 1, further comprising:
   a supporting plate attached to the one end of the probe body for supporting the gas permeable tube.

3. The tubing probe according to claim 2, wherein the supporting plate includes a plurality of holes to which the gas permeable tube is threaded.

4. The tubing probe according to claim 1, further comprising:
   tube adaptors attached at the one end of the probe body to which each end of the gas permeable tube is secured.

5. The tubing probe according to claim 4, further comprising:
   the tube adaptors are larger in the outside diameter than the inside diameter of the gas permeable tube.

6. The tubing probe according to claim 1, wherein the sealing mechanism includes the shoulder on the probe body and an O-ring, so that, when inserted, a standard fermenter nut port locks the probe in place and ensures that substantially only the gas permeable tube is located inside the enclosure and at the same time sterility of the enclosure.

7. The tubing probe according to claim 1, further comprising:
   a carrier gas supply tube connected to the inlet channel, and a volatile detector connected to the outlet channel.

8. The tubing probe according to claim 7, further comprising:
   the probe body having a head at another end, to which head a detachable detector head-set can be attached.

9. The tubing probe according to claim 1, wherein the gas permeable tube is made of a material which is permeable to a volatile of interest.

10. The tubing probe according to claim 9, wherein the gas permeable tube has its length and diameter which are chosen to optimise the performance of the probe in relation to the volatile of interest and environment in which to operate.

11. The tubing probe according to claim 9, wherein the material of the gas permeable tube is silicone.

12. The tubing probe according to claim 4, wherein each tube adaptor is configured in two sections, the tube section to receive one end of the gas permeable tube and another section to be welded to one end of the probe body.

13. The tubing probe according to claim 3, wherein the supporting plate has a plurality of holes so that a gas permeable tube of various length and size can be threaded.

14. The tubing probe according to claim 1, wherein the probe body is designed to fit in a standard 25 mm port of the enclosure.

15. The tubing probe according to claim 1, wherein the enclosure is a bioreactor or a fermenter.

* * * * *